US012643853B2

(12) United States Patent
Holland et al.

(10) Patent No.: US 12,643,853 B2
(45) Date of Patent: Jun. 2, 2026

(54) CANNABIGEROL PROLINE COCRYSTALS

(71) Applicant: Manoira Corporation, Tuxedo Park, NY (US)

(72) Inventors: Joanne Holland, Cambridge (GB); Alex Eberlin, Cambridge (GB)

(73) Assignee: MANOIRA CORPORATION, Tuxedo, NY (US)

( * ) Notice: Subject to any disclaimer, the term of this patent is extended or adjusted under 35 U.S.C. 154(b) by 1025 days.

(21) Appl. No.: 17/640,822

(22) PCT Filed: Sep. 4, 2020

(86) PCT No.: PCT/US2020/049334
§ 371 (c)(1),
(2) Date: Mar. 6, 2022

(87) PCT Pub. No.: WO2021/046303
PCT Pub. Date: Mar. 11, 2021

(65) Prior Publication Data

US 2022/0332682 A1 Oct. 20, 2022

Related U.S. Application Data

(60) Provisional application No. 62/896,868, filed on Sep. 6, 2019.

(51) Int. Cl.

| | |
|---|---|
| ***C07C 39/19*** | (2006.01) |
| ***A61K 31/00*** | (2006.01) |
| ***C07D 207/16*** | (2006.01) |

(52) U.S. Cl.
CPC .......... *C07D 207/16* (2013.01); *A61K 31/658* (2023.05); *C07C 39/19* (2013.01); *C07B 2200/13* (2013.01)

(58) Field of Classification Search
CPC ............................ C07C 39/19; C07B 2200/13
See application file for complete search history.

(56) References Cited

U.S. PATENT DOCUMENTS

| | | | |
|---|---|---|---|
| 9,815,810 B1 | 11/2017 | Ogilvie et al. | |
| 2015/0038567 A1 | 2/2015 | Herkenroth et al. | |
| 2016/0214920 A1 | 7/2016 | Roura | |
| 2019/0177258 A1 | 6/2019 | Emanuele et al. | |
| 2021/0380514 A1* | 12/2021 | Tesson | C07D 207/16 |

FOREIGN PATENT DOCUMENTS

WO 2020252369 A1 12/2020

OTHER PUBLICATIONS

Brittain et al. (H Brittain, ed. Polymorphism in Pharmaceutical Solids (1999) p. 235-238).*

Tilborg et al., "Pharmaceutical salts and cocrystals involving amino acids: A brief structural overview of the state-of-art," European Journal of Medicinal Chemistry 74: 411-426 (2014).

International Search Report in International Application PCT/US2020/49334, dated Feb. 3, 2021.

* cited by examiner

*Primary Examiner* — Valerie Rodriguez-Garcia
(74) *Attorney, Agent, or Firm* — Calfee, Halter & Griswold LLP

(57) ABSTRACT

Cannabigerol proline cocrystals are disclosed, specifically a 1:2 cannabigerol L-proline cocrystal, a 1:2 cannabigerol D-proline cocrystal and a 1:2 cannabigerol D, L-proline cocrystal and their preparation. Also disclosed are pharmaceutical compositions containing a cannabigerol proline cocrystal and a pharmaceutically acceptable excipient as well as methods and uses of a cannabigerol proline cocrystal or pharmaceutical composition to treat a disease, disorder or condition by administering to a patient in need thereof a therapeutically effective amount of a cannabigerol proline cocrystal or a pharmaceutical composition containing a cannabigerol proline cocrystal. Also disclosed are processes for the preparation of crystalline cannabigerol, Forms I, II and III.

5 Claims, 8 Drawing Sheets

CANNABIGEROL PROLINE COCRYSTALS

CROSS-REFERENCE TO RELATED APPLICATIONS

This application claims priority to U.S. application No. 62/896,868, filed Sep. 6, 2019, which is incorporated by reference.

FIELD OF THE INVENTION

The invention relates to cannabigerol proline cocrystals, therapeutic uses of the cannabigerol proline cocrystals and pharmaceutical compositions containing them.

BACKGROUND

*Cannabis* is the collective name for a series of plants belonging to the Cannabaceae family. Although *Cannabis* has been used for its medicinal purposes for centuries, in recent years, the potential benefits of the individual components that make up *Cannabis* have begun to be explored. *Cannabis* contains a large number of individual chemical compounds, one series of which is collectively known as phytocannabinoids. Despite the structural similarities of these molecules, each phytocannabinoid has very different pharmacological properties. In recent years the isolation of the individual cannabinoids has allowed scientists to determine their individual pharmacological properties and to explore their potential medicinal benefits. One of the cannabinoids that can be extracted from *Cannabis* is cannabigerol and despite the fact that this cannabinoid is only found in very small quantities in most *Cannabis* plants, its lack of psychoactivity combined with its numerous potential clinical applications has led to growing scientific interest in cannabigerol over recent years.

Cannabigerol, 2-[(2E)-3,7-dimethylocta-2,6-dienyl]-5-pentyl-benzene-1,3-diol, shown below, was first isolated and characterised in 1964 (Y. Gaoni. *Proc. Chem. Soc. Lond.* 1964; 82: 2189-2192).

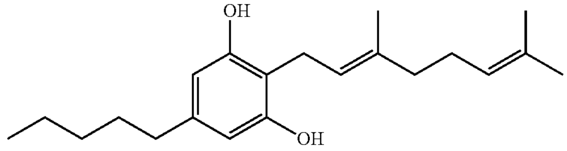

Cannabigerol

Since then its various pharmacological mechanisms have been explored and these have been found to include α2-adrenoceptor agonism and $5HT_{1A}$ receptor antagonism (M. G. Cascio. *Br. J. Pharmacol.* 210; 159: 129-141), endocannabinoid reuptake inhibition, TRPM8 receptor antagonism, TRPV1, TRPV2 and TRPA1 receptor agonism (L. De Petrocellis. *Br. J. Pharmacol.* 2011; 163(7); 1479-1494) as well as the ability to interact with CB1 and CB2 receptors (G. Navarro. Front. Pharmacol. 2018; 9: 632). Research also showed that cannabigerol may enhance PPARγ transcriptional activity (A. G. Granja. *J. Neuroimmune Pharmacol.* 2012; 7(4): 1002-1016). In a recent study it was shown that cannabigerol is a novel inhibitor of the enoyl acyl carrier protein (ACP) reductase (InhA) (L. Pinzi. *Molecules.* 2019; 24(14): 2567).

The wide-ranging pharmacological mechanisms of cannabigerol have led researchers to explore its medicinal potential in a range of conditions leading to numerous publications over recent years. Cannabigerol has been shown to possess neuroprotective properties in an experimental model of Huntington's disease opening up the potential to explore cannabigerol in the treatment of neurodegenerative diseases (S. Valdeolivas. *Neurotherapeutics.* 2015; 12(1): 185-199). It was also found that cannabigerol alters behavioural despair in an animal model of depression suggesting cannabigerol may have antidepressant effects (U.S. Pat. No. 841,085).

Due to the TRPM8 receptor antagonistic behaviour of cannabigerol researchers examined the potential of cannabigerol in carcinogenesis. It was found that cannabigerol hampers the progression of colon cancer in-vivo as well as inhibiting the growth of colorectal cancer cells in-vitro (F. Borrelli. *Carcinogenesis.* 2014; 35(12): 2787-2797). Cannabigerol was found to be an appetite stimulant in healthy rats, without neuromotor side effects (D. I. Brierley. *Psychopharmacology* (*Berl*). 2016; 233(19-20): 3603-3613) and was also shown to be able to attenuate chemotherapy induced cachexia in-vivo (D. I. Brierley. *J. Cachexia Sarcopenia Muscle.* 2019; 29).

Cannabigerol demonstrated protective and curative effects in a murine model of inflammatory bowel disease (F. Borelli. *Biochem. Pharmacol.* 2013; 85(9): 1306-1316), potentially, in part, explaining why *Cannabis* has previously been observed to have a beneficial effect on inflammatory bowel disease patients. It was found that cannabigerol had a strong effect on both mouse and human bladder contractility in-vitro suggesting a possible application in conditions associated with bladder dysfunction. Researchers have also demonstrated potential applications for cannabigerol in glaucoma (B. K. Colasanti. *Exp. Eye Res.* 1984; 39(3): 251-259) and psoriasis (J. D. Wilkinson. *J. Dermatol. Sci.* 2007; 45: 87-92).

Drug resistant tuberculosis has become a growing problem over recent years with these patients having limited treatment options. The recent discovery that cannabigerol is a potent inhibitor of the enoyl acyl carrier protein (ACP) reductase (InhA) could potentially open up a new treatment option for this infectious disease (L. Pinzi. *Molecules.* 2019; 24(14): 2567).

Given the number of medical conditions that have been identified as potential therapeutic targets for cannabigerol there is an important need to produce a pharmaceutical formulation of the cannabinoid that is suitable for carrying out human clinical trials. The chronic nature of several of these diseases requires a formulation that is convenient for regular dosing by the patient at home. Oral dosage forms, such as tablets, remain the dosage form of choice for the treatment of most conditions. They are convenient, cheaper to manufacture and facilitate simple and accurate dosing. Producing a solid oral dosage form from a drug substance requires the drug substance to be stable to formulation, processing and storage. Cannabigerol as extracted from the plant is an off-white to beige solid that has a melting point ~50° C. It has been found that on extraction cannabigerol typically exists as a mixture of two polymorphic forms. It is known that different polymorphic forms of a drug substance can have different chemical and physical properties, including melting point, apparent solubility, dissolution rate, mechanical properties, vapour pressure, and density. These properties have a direct effect on the manufacture of a drug product, as well as its stability, dissolution, and bioavailability. Thus, polymorphism can affect the quality, safety, and efficacy of a drug product. Drug regulatory bodies, such as the US FDA, require that the polymorphism of a drug is controlled in the manufacture and storage of a drug product so that there is no possibility of unexpected polymorphism changes occurring that could affect efficacy.

The inventors have found that recrystallization of cannabigerol from a solvent at different temperatures leads to the isolation of individual polymorphs. Recrystallization from heptane at room temperature produces a polymorph designated Form I (FIG. 6) whereas recrystallization from heptane at 5° C. produces the polymorph designated Form II (FIG. 7). Form II has previously been disclosed in U.S. Pat. No. 9,765,000 using a similar low temperature recrystallization of cannabigerol extracted from *Cannabis.*

The inventors have also found that the polymorph of cannabigerol that is isolated at room temperature (Form I) has a melting point of only 49° C. See Example 5 below. The formulation and processing methods typically used to form a solid oral dosage form (e.g. milling, compression, coating, etc) can often produce temperatures exceeding 49° C. Temperatures exceeding the melting point of the drug substance during drug product manufacture are problematic as this could lead to production of amorphous content, polymorphic changes or even degradation. When cannabigerol Form I was placed in an oven at 50° C. for only several minutes the cannabigerol became a liquid and on cooling XRPD analysis showed that the cannabigerol had undergone a form conversion to a previously unidentified polymorph (designated Form III). See Example 6 below and FIG. 8. The existence of multiple polymorphs of cannabigerol that interconvert under conditions typical of drug product manufacture suggest that cannabigerol in its free form would be unsuitable as a drug substance to be used in the manufacture of a solid form drug product as it is likely that it would not be possible to retain the consistent drug product quality required of a pharmaceutical product. There is, therefore, a need to find a new solid form of cannabigerol that has a melting point above temperatures reached during drug product formation and which does not exist in multiple polymorphic forms.

Alternative solid state forms of a drug that can be considered when developing a new pharmaceutical product include polymorphs, salts, cocrystals or solvates/hydrates. As discussed above and shown in Examples 5 and 6 below, cannabigerol exists in multiple polymorphic forms. The cannabigerol polymorphs are all low melting and readily interconvertible making them unsuitable for development. The structure of cannabigerol dictates that a strong base would be required to form a salt. Cannabigerol, however, is unstable to both acids and bases undergoing rapid degradation (L. O. Hanus. *Nat. Prod. Rep.* 2016; 33: 1357-1392) making salt formation an unsuitable option. No solvate or hydrate forms of cannabigerol have been observed. Due to these difficulties there is a need in the art for a stable cannabigerol composition that makes pharmaceutical development and use possible.

SUMMARY OF THE INVENTION

The invention relates to cannabigerol proline cocrystals, specifically a 1:2 cannabigerol L-proline cocrystal, a 1:2 cannabigerol D-proline cocrystal and a 1:2 cannabigerol D,L-proline cocrystal.

The invention also relates to pharmaceutical compositions containing a cannabigerol proline cocrystal of the invention and a pharmaceutically acceptable excipient.

The invention further relates to methods and uses of a cannabigerol proline cocrystal or pharmaceutical composition to treat various diseases, disorders or conditions by administering to a patient in need thereof a therapeutically effective amount of a cannabigerol proline cocrystal of the invention or a pharmaceutical composition containing a cannabigerol proline cocrystal of the invention.

The invention also relates to the preparation of polymorphic forms I-III of cannabigerol.

DESCRIPTION OF THE INVENTION

Figure 1:
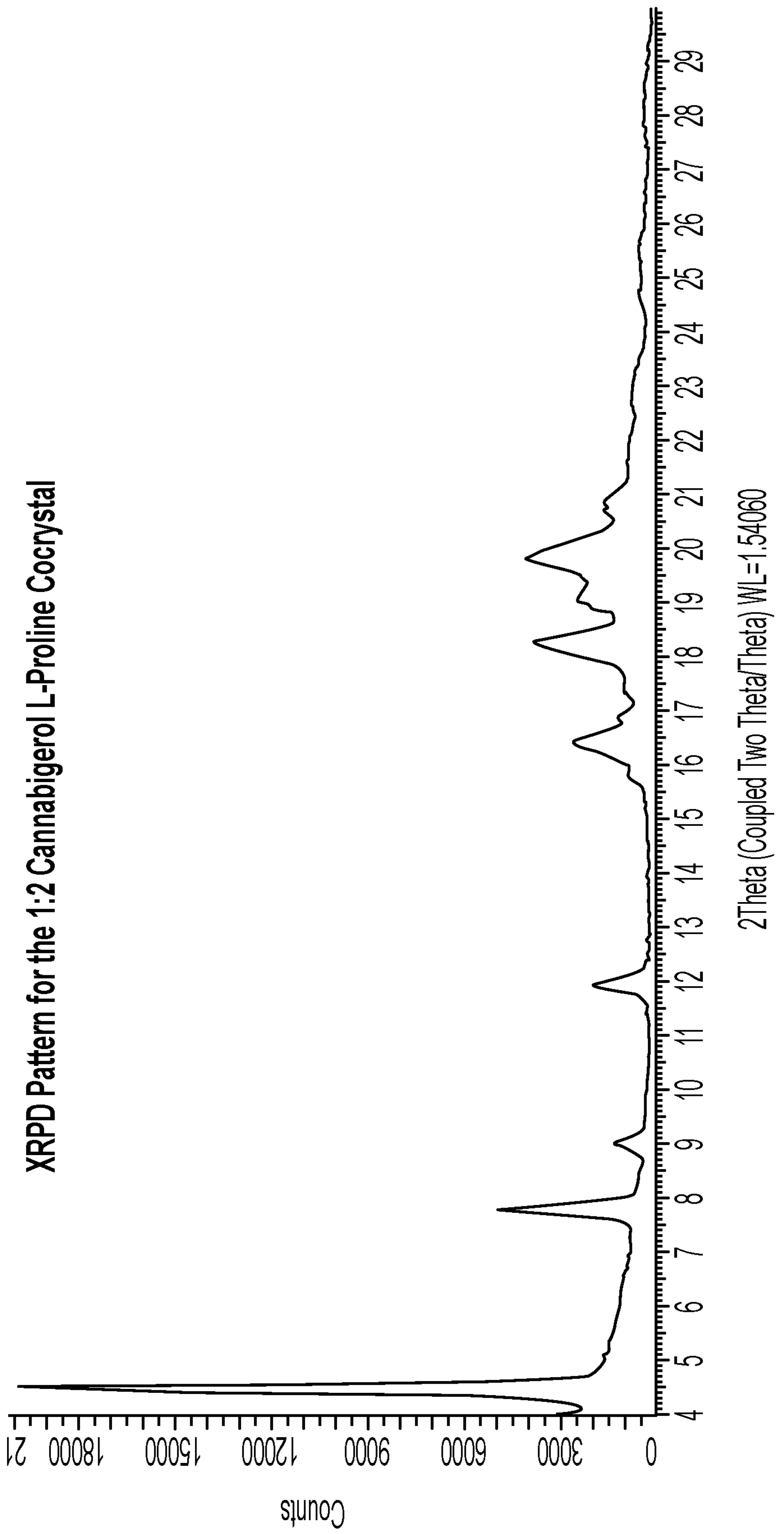
FIG. 1 depicts the XRPD pattern for the 1:2 cannabigerol L-proline cocrystal.

The invention relates to cannabigerol proline cocrystals, specifically a 1:2 cannabigerol L-proline cocrystal, a 1:2 cannabigerol D-proline cocrystal and a 1:2 cannabigerol D,L-proline cocrystal. These cannabigerol proline cocrystals of the invention, their preparation and their characterization are described in the examples below and shown in the figures. The invention relates to pharmaceutical compositions containing a therapeutically effective amount of a cannabigerol proline cocrystal of the invention and a pharmaceutically acceptable carrier. The invention also relates to methods of treatment for the diseases, disorders and conditions described herein and the use of a therapeutically effective amount of a cannabigerol proline cocrystal of the invention, or a pharmaceutical composition containing it, for that treatment. The invention further provides the use of a cannabigerol proline cocrystal of the invention in the manufacture of a medicament for use in the treatment of the diseases, disorders and conditions described herein.

The invention also relates to the preparation of cannabigerol proline cocrystals, specifically a 1:2 cannabigerol L-proline cocrystal, a 1:2 cannabigerol D-proline cocrystal and a 1:2 cannabigerol D,L-proline cocrystal. as shown in the examples.

In another embodiment the invention relates to processes for the preparation of crystalline cannabigerol Forms I, II and III. Crystalline form III is a novel polymorph of cannabigerol. Crystalline Form I of cannabigerol is prepared by stirring cannabigerol in heptane at ambient temperature for a time sufficient, e.g. 1-24 hours or 10-20 hours, to precipitate crystalline Form I of cannabigerol. Crystalline Form II of cannabigerol is prepared by storing cannabigerol in hexanes at 5° C. for a time sufficient, e.g. 1-72 hours or 24-48 hours, to precipitate crystalline Form II of cannabigerol. Crystalline Form III of cannabigerol is prepared by heating cannabigerol at 50° C. for a time sufficient, e.g. 1-20 minutes or 5-15 minutes, to melt the cannabigerol and allowing the melt to cool to form crystalline Form III of cannabigerol. The novel crystalline form III of cannabigerol has an X-ray powder diffraction pattern substantially similar to FIG. 8.

Therapeutic Uses of Cannabigerol Proline Cocrystals

As discussed above cannabigerol is known in the art to be useful in the treatment of various diseases, disorders and conditions. The cannabigerol proline cocrystals of the invention, 1:2 cannabigerol L-proline cocrystal, 1:2 cannabigerol D-proline cocrystal and 1:2 cannabigerol D,L-proline cocrystal, and pharmaceutical compositions containing them may then also be used to treat such diseases, disorders and conditions. The diseases, disorders or conditions which may treated with a cannabigerol proline cocrystal of the invention include, but are not limited to: pain (including but not limited to acute pain; chronic pain; neuropathic pain and cancer pain), neurodegenerative disease (including but not limited to Alzheimer's disease; Parkinson's disease; amyotrophic lateral sclerosis; Huntington's disease; multiple sclerosis; frontotemporal dementia; prion disease; Lewy body dementia; progressive supranuclear palsy; vascular dementia; normal pressure hydrocephalus; traumatic spinal cord injury; HIV dementia; alcohol induced neurotoxicity; Down's syndrome; epilepsy or any other related neurological or psychiatric neurodegenerative disease), ischemic disease (including but not limited to stroke; cardiac ischemia; coronary artery disease; thromboembolism; myocardial infarction or any other ischemic related disease), brain injury or damage (including but not limited to traumatic brain injury is taken from the group: diffuse axonal injury; concussion; contusion; whiplash or any other traumatic head or brain injury), acquired brain injury (including but not limited to stroke; anoxic brain injury; hypoxic brain injury or any other acquired brain injury), age related inflammatory or autoimmune disease, inflammatory bowel disease, bladder dysfunction, cachexia (including related conditions such as AIDS wasting disease, weight loss associated with cancer, chronic obstructive pulmonary disease or infectious diseases such as tuberculosis), appetite suppression, nausea and vomiting, glaucoma, movement disorders, rheumatoid arthritis, asthma, allergy, psoriasis, Crohn's disease, systemic lupus erythematosus, diabetes, cancer (including colon and colorectal cancer), osteoporosis, renal ischemia and nephritis.

Accordingly, the invention relates to the method of treating such a disease, disorder, or condition comprising the step of administering to a patient in need thereof a therapeutically effective amount of a cannabigerol proline cocrystal of the invention or of administering to a patient in need thereof a therapeutic composition containing a cannabigerol proline cocrystal of the invention.

The term "treatment" or "treating" means any treatment of a disease, disorder or condition in a mammal, including: preventing or protecting against the disease, disorder or condition, that is, causing the clinical symptoms not to develop; inhibiting the disease, disorder or condition, that is, arresting or suppressing the development of clinical symptoms; and/or relieving the disease, disorder or condition (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the disease, disorder or condition. The term "protection" is meant to include "prophylaxis."

Another aspect of the invention relates to the use of a cannabigerol proline cocrystal of the invention in the treatment of diseases, disorders and conditions discussed above. Accordingly, the invention further relates to the manufacture of a medicament for use in the treatment of such diseases, disorders and conditions.

Pharmaceutical Compositions Containing Cannabigerol Proline Cocrystals

The invention also relates to pharmaceutical compositions comprising, consisting essentially or consisting of a therapeutically effective amount of a cannabigerol proline cocrystal according to the invention and a pharmaceutically acceptable carrier (also known as a pharmaceutically acceptable excipient). As mentioned above, these pharmaceutical compositions are therapeutically useful to treat or prevent disorders such as those discussed above. A pharmaceutical composition of the invention may be a solid dosage form or a solution made with a cannabigerol proline cocrystal of the invention.

A pharmaceutical composition of the invention may be in any pharmaceutical form which contains or is made from a cannabigerol proline cocrystal according to the invention. The pharmaceutical composition may be, for example, a tablet, a capsule, an oral solution, an injectable composition, a topical composition, an inhalable composition or a transdermal composition. Liquid pharmaceutical compositions may be prepared using a cannabigerol proline cocrystal of the invention and represent a particular embodiment of the invention. For a liquid pharmaceutical composition, the cannabigerol proline cocrystal may be dissolved in a solvent, e.g. water, at the time and point of care.

The pharmaceutical compositions generally contain, for example, about 0.1% to about 99.9% by weight of a cannabigerol proline cocrystal of the invention, for example, about 0.5% to about 99% by weight of a cannabigerol proline cocrystal of the invention and, for example, 99.5% to 0.5% by weight of at least one suitable pharmaceutical excipient or solvent. In one embodiment, the composition may be between about 5% and about 75% by weight of a cannabigerol proline cocrystal of the invention with the rest being at least one suitable pharmaceutical excipient, solvent or at least one other adjuvant, as discussed below.

A "therapeutically effective amount of a cannabigerol proline cocrystal according to the invention" is that which correlates to a therapeutic effect and may for example, be about 5 mg-about 2,000 mg, about 50 mg-about 1500 mg, about 100 mg-about 1000 mg, about 250 mg-about 750 mg, or about 500 mg. The actual amount required for treatment of any particular disease, disorder or condition for any particular patient may depend upon a variety of factors including, for example, the particular disease, disorder or condition being treated; the disease state being treated and its severity; the specific pharmaceutical composition employed; the age, body weight, general health, sex and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used. For a solid pharmaceutical composition of the invention, that is one containing a cannabigerol proline cocrystal of the invention, a carrier should be chosen that maintains the crystalline form. In other words, the carrier should not substantially alter a cannabigerol proline cocrystal. Nor should the carrier be otherwise incompatible with a cannabigerol proline cocrystal used, such as by producing any undesirable biological effect or otherwise interacting in a deleterious manner with any other component(s) of the pharmaceutical composition.

The pharmaceutical compositions of the invention may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, a cannabigerol proline cocrystal of the invention may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others, as is known in the pharmaceutical art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

A pharmaceutical composition of the invention may be formulated as a chewable lozenge, also known as a gummy-type lozenge. As is known in the art, chewable lozenge formulations may be prepared from glycerin, gelatin, and water. The lozenges typically also contain a flavorant such as a fruit or candy flavor and a colorant to give the formulation a pleasant flavor and appearance. Chewable lozenges may also be made or molded into a variety of shapes such as, but not limited to, ovoid, spherical, platonic solids (e.g. tetrahedrons, cubes, octahedrons, etc.), rectangular prisms, cones, pyramids, cylinders, fruit slices, animals, cartoon characters, cars, etc. An exemplary chewable lozenge of the invention may contain: a desired amount of the cocrystal, glycerin, gelatin, water, methylparaben, flavoring oil, and a colorant.

A pharmaceutical composition of the invention may also be formulated as a sublingual or buccal preparation—a tablet form not used as often as oral tablets. These small, hard compressed tablets are designed to dissolve rapidly in the vascular mucous membrane of the mouth. Buccal tablets are placed in the buccal pouch (between the check and the gum) and sublingual tablets are placed under the tongue. Because the buccal and sublingual areas are highly vascularized, drugs are quickly absorbed into the bloodstream with rapid onset of the drug effects. Drugs administered in this way avoid first-pass metabolism because the adsorbed drug bypasses the portal vein unlike drugs adsorbed from the gastrointestinal (GI) tract. Sublingual and buccal formulations may be prepared using pharmaceutically acceptable carriers and disintegrants known in the art as well as flavorants and other additives to improve taste and patient acceptance and compliance.

Inhalable formulations may be used to administer the cocrystal of the invention topically to the lung or within the nasal passages. One inhalable formulation is a dry powder inhaler formulation of respirable particles comprised of the cocrystal of the invention, which the patient being treated inhales. It is common for a dry powder formulation to include carrier particles, to which the cocrystal particles can adhere to. The carrier particles may be of any acceptable pharmacologically inert material or combination of materials. For example, the carrier particles may be composed of one or more materials selected from sugar alcohols; polyols, for example sorbitol, mannitol or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose. The cocrystal would be dispersed into the respiratory tract in a pharmaceutically effective amount.

Pharmaceutical compositions for rectal administrations are, for example, suppositories that may be prepared by mixing a cannabigerol proline cocrystal of the invention with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Pharmaceutical compositions suitable for topical administration include liquid or semi-liquid preparations such as liniments, lotions, gels, applicants, oil-in-water or water-in-oil emulsions such as creams, ointments, pastes or foams; or solutions or suspensions such as drops, as is known in the art. Compositions of the invention may be intended for topical administration, in which case the carrier may suitably comprise a solution, emulsion, ointment or gel base. The carrier or base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

In addition to the topical method of administration described above, there are various methods of administering the active a cannabigerol proline cocrystal of the invention topically to the lung. One such means could involve a dry powder inhaler formulation of respirable particles comprised of a cannabigerol proline cocrystal of the invention, which the patient being treated inhales. It is common for a dry powder formulation to include carrier particles, to which cannabigerol proline cocrystal particles can adhere to. The carrier particles may be of any acceptable pharmacologically inert material or combination of materials. For example, the carrier particles may be composed of one or more materials selected from sugar alcohols; polyols, for example sorbitol, mannitol or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose.

In addition to the topical method of administration described above, there are various methods of administering the active a cannabigerol proline cocrystal of the invention systemically by such methods. One such means would involve an aerosol suspension of respirable particles comprised of a cannabigerol proline cocrystal of the invention, which the patient being treated inhales. A cannabigerol proline cocrystal would be absorbed into the bloodstream via the lungs in a pharmaceutically effective amount. The respirable particles can be liquid or solid, with a particle size sufficiently small to pass through the mouth and larynx upon inhalation.

Because the crystalline form of a cannabigerol proline cocrystal may be maintained during preparation, solid dosage forms are one embodiment of the pharmaceutical composition of the invention. Dosage forms for oral administration, which includes capsules, tablets, pills, powders, granules, and suspensions may be used. Dosage forms for pulmonary administration, which includes metered dose inhaler, dry powder inhaler or aerosol formulations may be used. In such solid dosage forms, the active compound may be mixed with at least one inert, pharmaceutically acceptable excipient (also known as a pharmaceutically acceptable carrier).

A cannabigerol proline cocrystal according to the invention may also be used to formulate liquid or injectable pharmaceutical compositions. Administration of a cannabigerol proline cocrystal in pure form or in an appropriate pharmaceutical composition may be carried out via any of the accepted modes of administration or agents for serving similar utilities. Thus, administration may be, for example, orally, buccally, nasally, pulmonary, parenterally (intravenous, intramuscular, or subcutaneous), topically, transdermally, intravaginally, intravesically, intrasystemically, ophthalmically or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

The invention also relates to a method of preparing a liquid pharmaceutical composition comprising the step of dissolving a cannabigerol proline cocrystal according to the invention in a pharmaceutically acceptable solvent and to liquid pharmaceutical compositions prepared according to that method. As discussed above, liquid pharmaceutical compositions of the invention may be administered orally, parenterally (including by inhalation), and intravenously.

EXAMPLES

The following analytical methods were used to characterize the 1:2 cannabigerol L-proline cocrystal of the invention:

X-Ray Powder Diffraction Characterisation: X-ray powder diffraction patterns for the samples were acquired on a Bruker D8 diffractometer using CuKα radiation (40 kV, 40 mA), θ-2θ goniometer, V4 receiving slits, a Ge monochromator and a Lynxeye detector. The instrument is performance checked using a certified Corundum standard (NIST 1976). The data were collected over an angular range of 4° to 30° 2Θ using a step size of 0.05° 2Θ and a step time of 4 seconds. Samples were run under ambient conditions as flat plate specimens using powder as received. Approximately, 35 mg of the sample was gently packed into a cavity cut into polished, zero background (510) silicon wafer. The software used for data collection and analysis was Diffrac Plus XRD Commander and Diffrac Plus EVA respectively.

Fourier Transform Infrared (FT-IR) Characterisation FT-IR spectra were acquired using a Perkin Elmer Spectrum 2 spectrometer, collecting between 450 $cm^{-1}$ and 4000 $cm^{-1}$ using 4 scans and a resolution of 4 $cm^{-1}$. A Universal ATR diamond accessory was used and the data was collected using software version NIOS2 main 00.02.0064. Analysis of the data was carried out using Spectrogryph version 1.2.9.

Thermal Analysis—Differential Scanning calorimetry (DSC): DSC data were collected on a PerkinElmer Pyris 4000 DSC. The instrument was verified for energy and temperature calibration using certified indium. A predefined amount of the sample, 0.5-3.0 mg, was placed in a pin holed aluminium pan and heated at 20° C.·$min^{-1}$ from 30 to 350° C. The instrument control, data acquisition and analysis were performed with Pyris Software v9.0.1.0203.

Thermo-Gravimetric Analysis (TGA): TGA data were collected on a PerkinElmer Pyris 1 TGA equipped with a 20-position auto-sampler. The instrument was calibrated using a certified weight and certified Alumel and Perkalloy for temperature. A predefined amount of the sample, 1-5 mg, was loaded onto a pre-tared aluminium crucible and was heated at 20° C.·$min^{-1}$ from ambient temperature to 400° C. A nitrogen purge at 20 ml·$min^{-1}$ was maintained over the sample. The instrument control, data acquisition and analysis were performed with Pyris Software v9.0.1.0203.

Cannabigerol Polymorph X-Ray Powder Diffraction Characterisation: X-ray powder diffraction patterns for the samples were acquired on a Bruker 2nd Gen D2-Phaser diffractometer using CuKα radiation (30V, 10 mA), θ-2θ goniometer, V4 receiving slits, a Ge monochromator and Lynxeye detector. The instrument is performance checked using a certified Corundum standard (NST 1976). The data were collected at ambient temperature over an angular range of 2° to 35° 2Θ (using a step size of 0.05° 2Θ and a step time of 2.0 seconds), Samples run under ambient conditions were prepared as flat plate specimens using powder, approximately, 20 mg of the sample was gently packed into sample holder and all samples were analysed using Diffrac Plus EVA v4.2.0.14

Example 1: 1:2 Cannabigerol L-Proline Cocrystal

1.1 Preparation of a 1:2 Cannabigerol L-Proline Cocrystal

The batch of the 1:2 cannabigerol L-proline cocrystal used for characterisation was prepared as follows:

Cannabigerol (426 mg) and L-proline (280 mg) were added to a 50 ml round-bottom (RB) flask and 20 ml of nitromethane was added. The slurry was heat/cool cycled between 50° C. and room temperature (8 hours—4 hours heating to 50° C. and then 4 hours cooling to room temperature) for 3 days. The product was then filtered and dried in a vacuum oven at 30° C. overnight.

1.2 XRPD Characterisation of the 1:2 Cannabigerol L-Proline Cocrystal

The experimental XRPD pattern of the 1:2 cannabigerol L-proline cocrystal is shown in FIG. 1. Table 1 lists the angles, ° 2θ±0.2° 2θ, and d value of the peaks identified in the experimental XRPD pattern of FIG. 1. The entire list of peaks or corresponding d values, or a subset thereof, may be sufficient to characterize the cocrystal, as well as by an XRPD pattern substantially similar to FIG. 1.

For example, a 1:2 cannabidiol:L-proline cocrystal of the invention may be characterized by an X-ray powder diffraction pattern having at least two peaks selected from 4.5, 7.8, 18.3 and 19.8° 2θ±0.2°2θ.

TABLE 1

| Angle °2θ ± 0.2 °2θ | d value Angstrom | Intensity % |
|---|---|---|
| 4.5 | 19.69 | 100.0% |
| 7.8 | 11.33 | 25.1% |
| 9.0 | 9.81 | 5.6% |
| 11.9 | 7.40 | 10.1% |
| 15.8 | 5.60 | 2.8% |
| 16.4 | 5.41 | 12.4% |
| 16.8 | 5.27 | 4.0% |
| 18.3 | 4.86 | 18.8% |
| 19.1 | 4.65 | 10.9% |
| 19.8 | 4.48 | 20.4% |
| 20.7 | 4.29 | 5.9% |

1.3 Infrared Spectrum of the 1:2 Cannabigerol L-Proline Cocrystal

Figure 2:
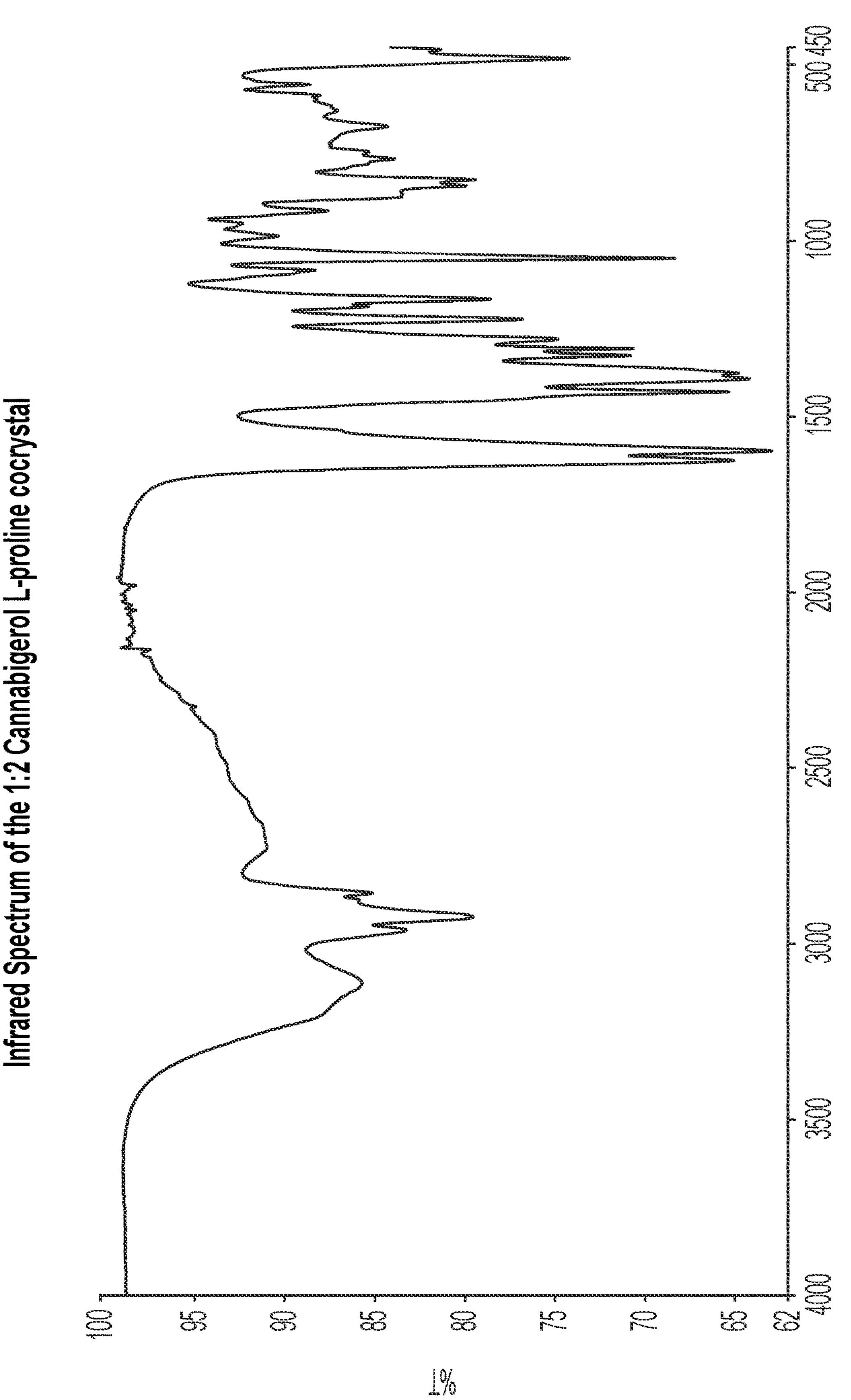
FIG. 2 depicts the infrared spectrum of the 1:2 cannabigerol L-proline cocrystal.

The experimental Infrared Spectrum of the 1:2 cannabigerol L-proline cocrystal is shown in FIG. 2. The significant peaks identified in the experimental infrared spectrum of FIG. 2 are 3112, 2960, 2923, 2856, 1625, 1597, 1429, 1393, 1376, 1326, 1307, 1280, 1224, 1166, 1050, 950, 843, 826, 767, 746, 675, 482 and 456 $cm^1$±1 $cm^1$. The entire list of peaks, or a subset thereof, may be sufficient to characterize the cocrystal, as well as by an infrared spectrum substantially similar to FIG. 2. For example, the 1:2 cannabigerol L-proline cocrystal may be characterized by at least four peaks selected from the peaks at 1625, 1597, 1429, 1307, 1280, 1224, 1166 and 1050 $cm^{-1}$±1 $cm^{-1}$.

1.4 DSC of the 1:2 Cannabigerol L-Proline Cocrystal

Figure 3:
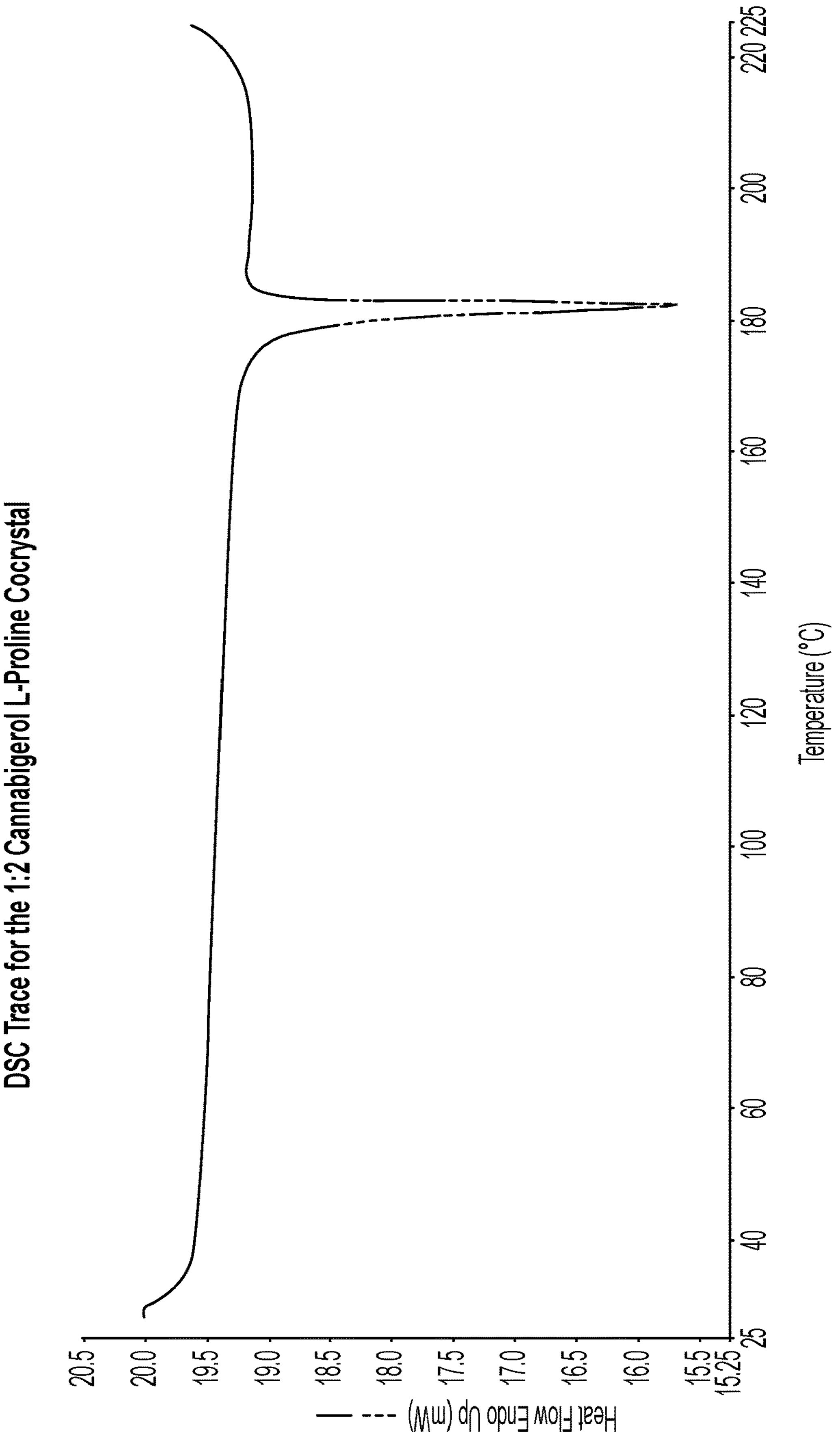
FIG. 3 depicts the DSC trace for the 1:2 cannabigerol L-proline cocrystal.

The differential scanning calorimetry (DSC) trace, FIG. 3, shows a single endotherm with a peak maximum of 182.4° C.

1.5 TGA of the 1:2 Cannabigerol L-Proline Cocrystal

Figure 4:
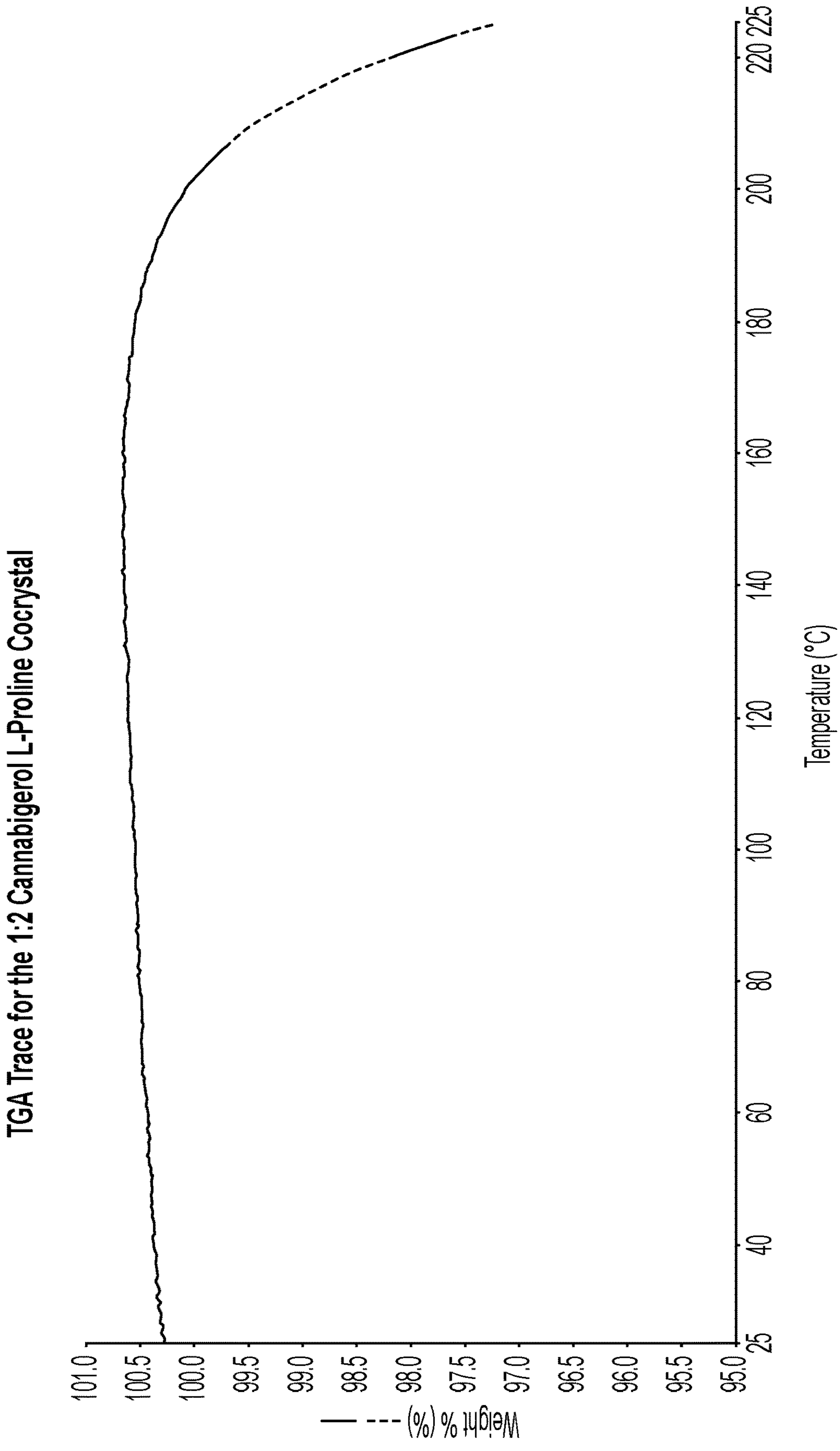
FIG. 4 depicts the TGA trace for the 1:2 cannabigerol L-proline cocrystal.

The thermal gravimetric analysis (TGA) trace, FIG. 4, shows no significant weight loss prior to 210° C.

1.6 $^1$H NMR Spectrum of the 1:2 Cannabigerol L-Proline Cocrystal

Figure 5:
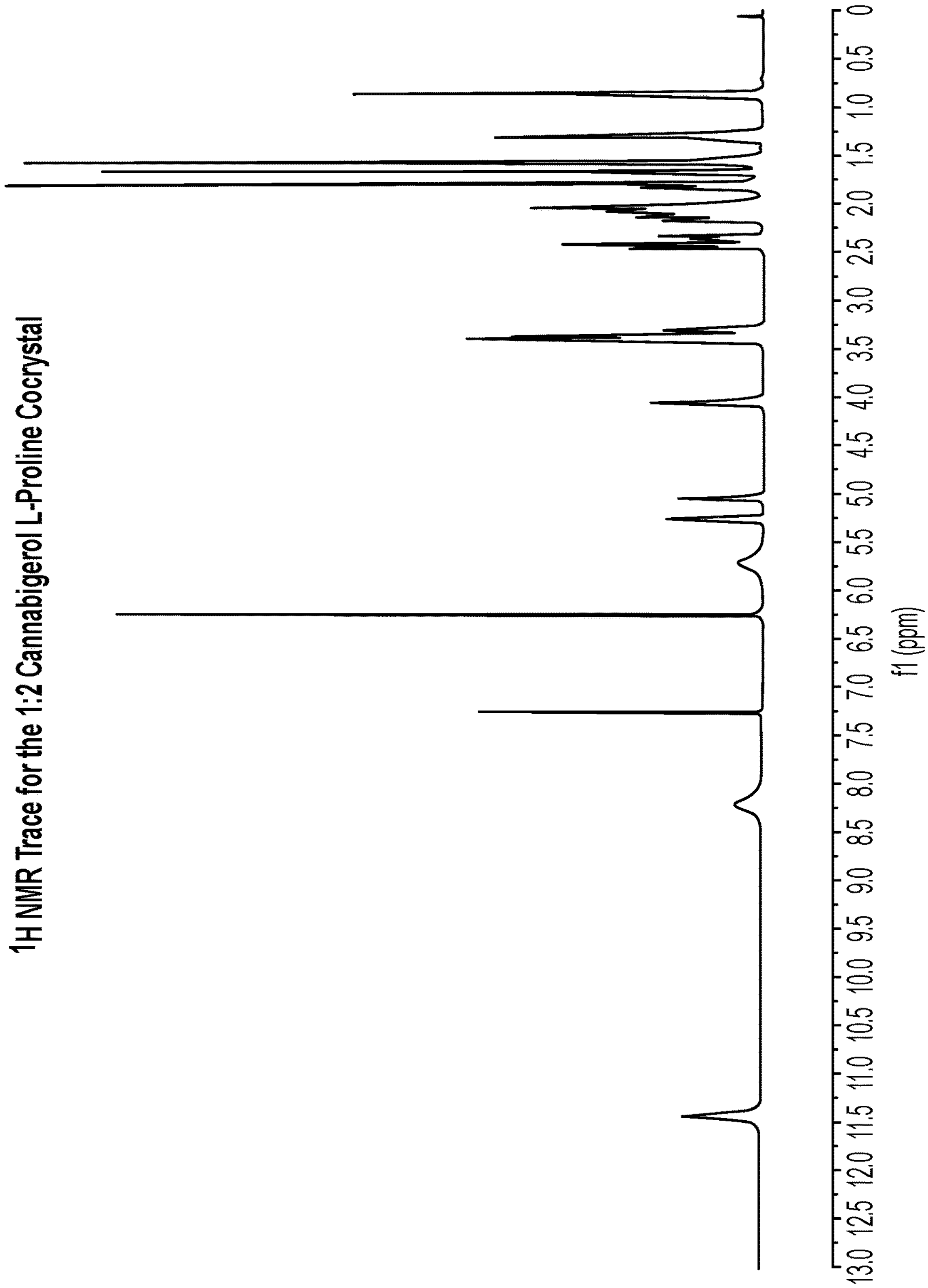
FIG. 5 depicts the $^1$H NMR trace for the 1:2 cannabigerol L-proline cocrystal.

The $^1$H NMR spectrum of the 1:2 cannabigerol L-proline cocrystal, shown in FIG. 5, displays the following peaks (interchangeable protons are not included): $^1$H NMR (400 MHz, $CDCl_3$) 0.87 (t, 3H), 1.23-1.36 (m, 4H), 1.48-1.62 (m, 5H), 1.67 (s, 3H), 1.78-1.88 (m, 5H), 1.95-2.20 (m, 8H), 2.30-2.49 (m, 4H), 3.20-3.50 (m, 6H), 4.05 (br s 2H), 5.05 (t, 1H), 5.26 (t, 1H), 5.71 ppm (br s, 1H) and 6.24 (s, 2H). The peak at 4.05 ppm in the $^1$H NMR spectrum corresponds to one proton on the pyrrolidine ring of L-proline. Comparison of the integration of this peak with that at 6.24 ppm, which corresponds to two protons on the aromatic ring of cannabigerol, indicates that the cocrystal has a cannabigerol: L-proline stoichiometry of 1:2.

Example 2: Solid-State Stability Study for the 1:2 Cannabigerol L-Proline Cocrystal A study was carried out to examine the physical stability of the 1:2 cannabigerol L-proline cocrystal with respect to solid form conversion or deliquescence over time under accelerated conditions. 1:2 Cannabigerol L-proline cocrystal (50 mg) was placed in a sealed container at 40° C. and 75% relative humidity and stored under these conditions for 8 weeks. After this time the sample was found to be completely solid with no signs of deliquescence. The sample was analysed by XRPD to observe any potential form changes. XRPD analysis showed that the 1:2 cannabigerol L-proline cocrystal retained its original crystalline form and that no solid form conversion occurred under these conditions.

A second study was carried out to explore the solid-state stability of the 1:2 cannabigerol L-proline cocrystal under high storage temperatures. 1:2 cannabigerol L-proline cocrystal (50 mg) was stored in an oven at 100° C. for 20 hours. After this time the sample was analysed by XRPD to observe any potential form changes. XRPD analysis showed that the 1:2 cannabigerol L-proline cocrystal retained its original crystalline form and that no solid form conversion had occurred under these conditions.

Example 3: 1:2 Cannabigerol D-Proline Cocrystal

The batch of the 1:2 cannabigerol D-proline cocrystal used for characterisation was prepared as follows:

Cannabigerol (426 mg) and D-proline (280 mg) were added to a 50 ml round-bottom (RB) flask and 20 ml of nitromethane was added. The slurry was heat/cool cycled between 50° C. and room temperature (8 hours—4 hours heating to 50° C. and then 4 hours cooling to room temperature) for 3 days. The product was then filtered and dried in a vacuum oven at 30° C. overnight. The sample was analysed by XRPD, DSC, TGA and $^1$H NMR and was found to be indistinguishable under these analytical techniques from the 1:2 cannabigerol L-proline cocrystal and therefore may be characterized as described for the 1:2 cannabigerol L-proline cocrystal in Example 1.

Example 4: 1:2 Cannabigerol D,L-proline Cocrystal

The batch of the 1:2 cannabigerol D,L-proline cocrystal used for characterisation was prepared as follows:

Cannabigerol (426 mg) and D,L-proline (280 mg) were added to a 50 ml round-bottom (RB) flask and 20 ml of nitromethane was added. The slurry was heat/cool cycled between 50° C. and room temperature (8 hours—4 hours heating to 50° C. and then 4 hours cooling to room temperature) for 3 days. The product was then filtered and dried in a vacuum oven at 30° C. overnight. The sample was analysed by XRPD, DSC, TGA and $^1$H NMR and was found to be indistinguishable under these analytical techniques from the 1:2 cannabigerol L-proline cocrystal and therefore may be characterized as described for the 1:2 cannabigerol L-proline cocrystal in Example 1.

Example 5: Cannabigerol Polymorph Isolation

Figure 6:
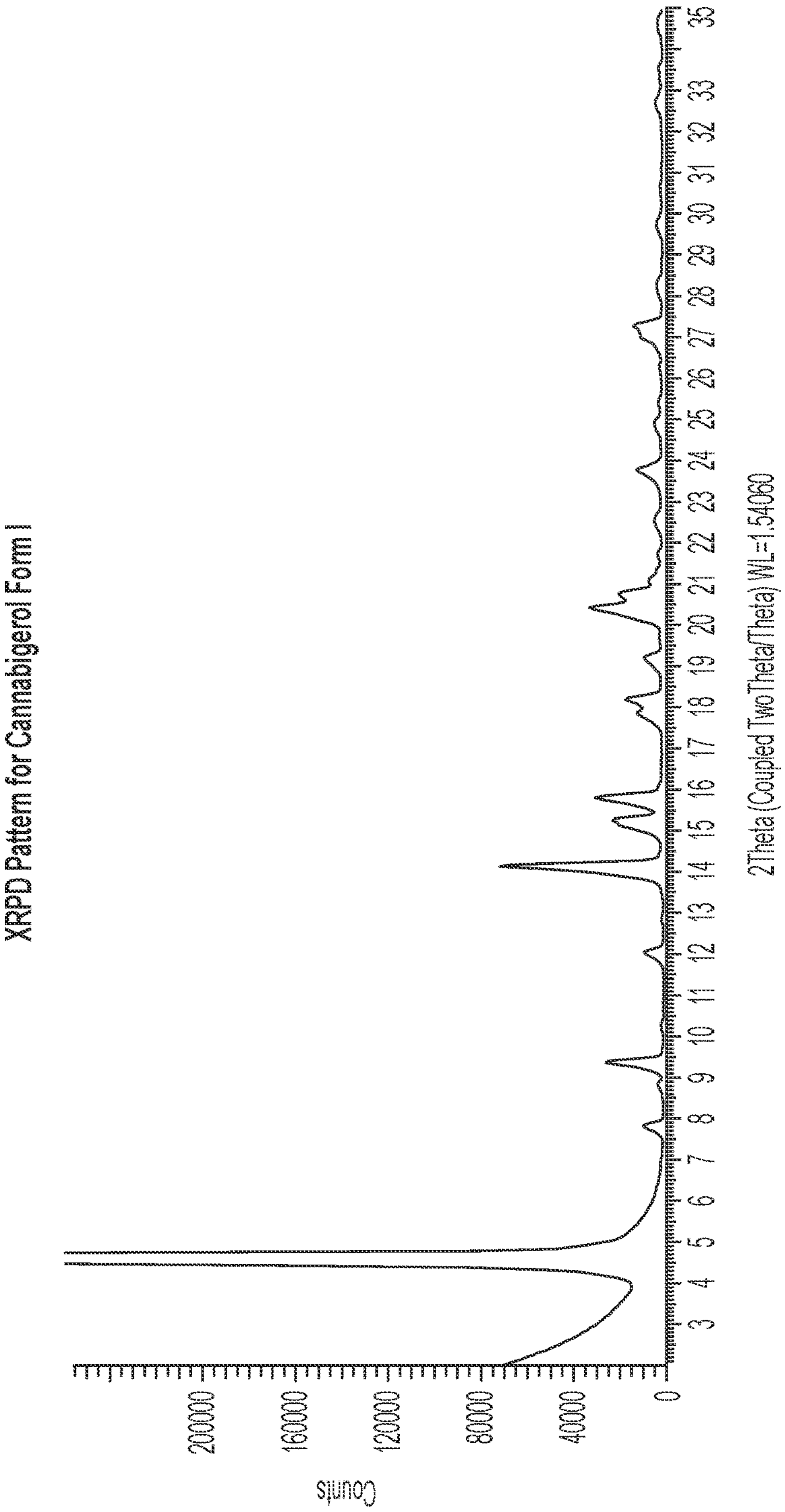
FIG. 6 depicts the XRPD pattern for cannabigerol form I.

As cannabigerol extracted directly from hemp consisted of a mixture of Forms I and II recrystallization studies were carried out to try to isolate the individual polymorphs. Cannabigerol (875 mg, 2.76 mmol) was stirred at room temperature in heptane (10 ml) for 20 hours. The resulting solid was and filtered and dried under ambient conditions. XRPD analysis confirmed the product to be cannabigerol Form I. The XRPD for cannabigerol Form I is shown in FIG. 6.

Figure 7:
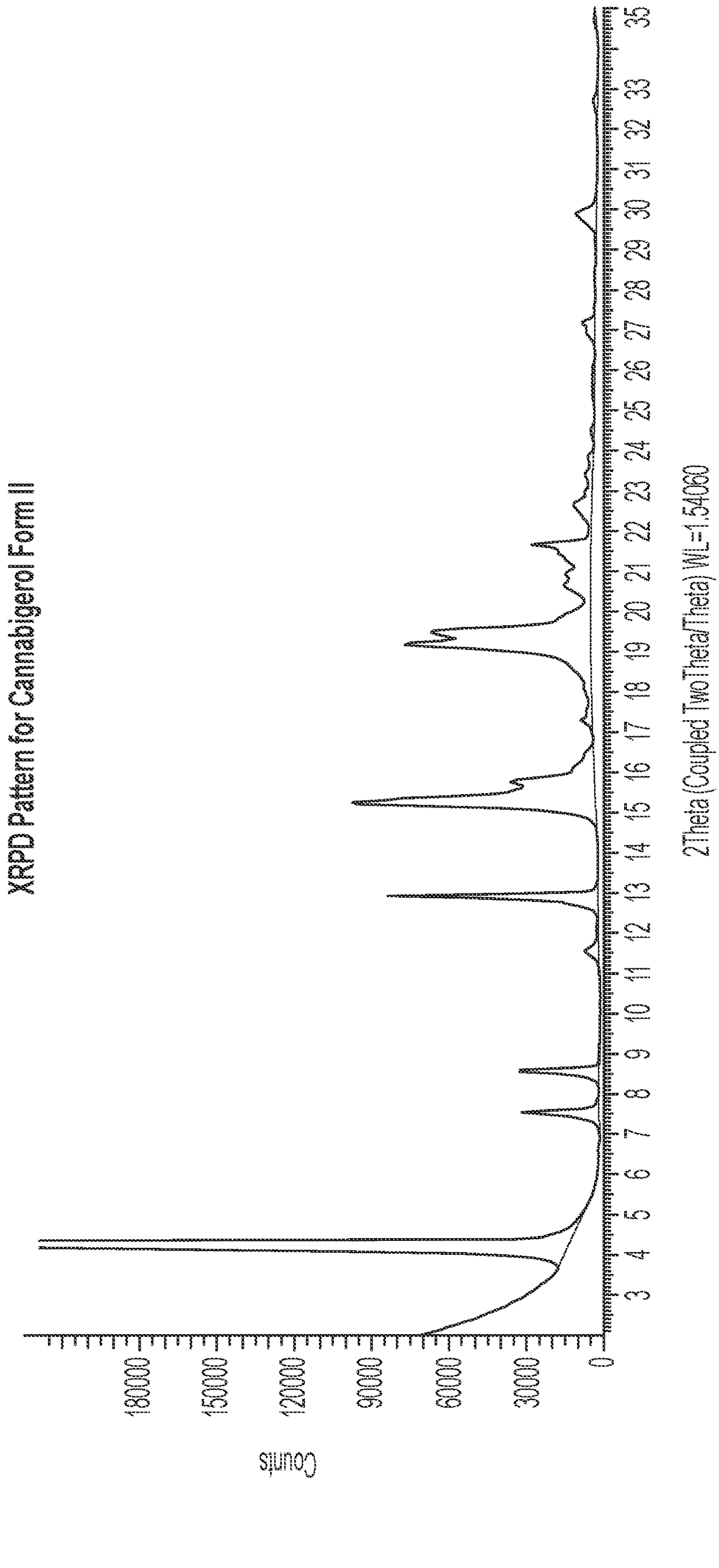
FIG. 7 depicts the XRPD pattern for cannabigerol form II.

The clear liquors from the above filtration were stored at 5° C. for 48 hours. The resulting white precipitate was filtered and dried under ambient conditions. XRPD analysis confirmed the product to be cannabigerol Form II. The XRPD for cannabigerol Form II is shown in FIG. 7.

Example 6: Solid-State Stability of Cannabigerol Form I

Figure 8:
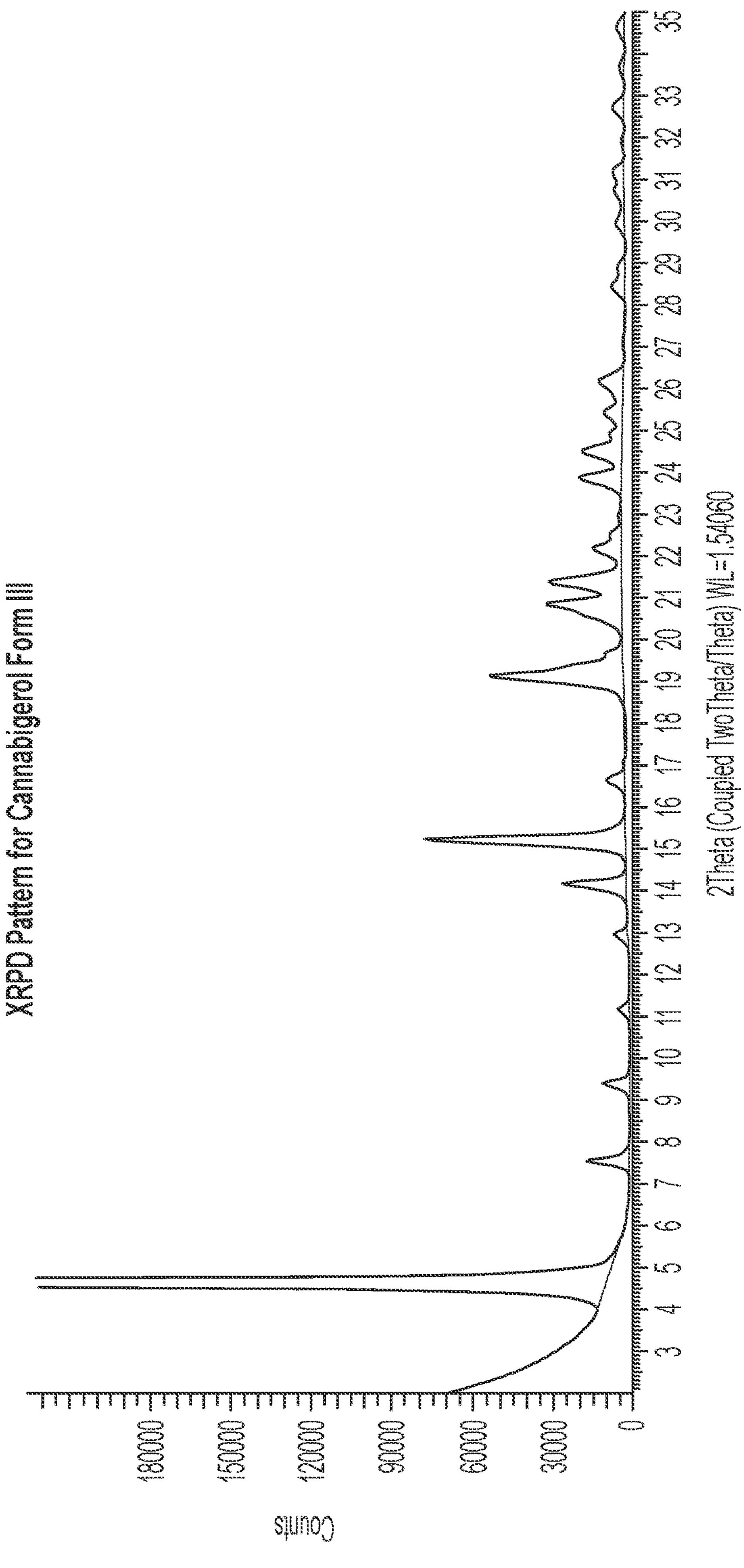
FIG. 8 depicts the XRPD pattern for cannabigerol form III.

A study was carried out to assess the stability of cannabigerol Form I under conditions of temperatures commonly reached during processing and storage. Cannabigerol Form I (50 mg) was placed in an oven at 50° C. for 10 minutes. After this time the sample had melted to produce an oil. The sample was allowed to cool after which time a solid was produced. XRPD analysis of the sample showed that the cannabigerol had undergone a polymorph transition to form a new polymorphic form (designated Form III). The experimental XRPD pattern for the cannabigerol Form III is shown in FIG. 8.

The claimed invention is:

1. A cannabigerol proline cocrystal selected from the group of 1:2 cannabigerol L-proline cocrystal, 1:2 cannabigerol D-proline cocrystal and 1:2 cannabigerol D, L-proline cocrystal; wherein the cannabigerol proline cocrystal is characterized by:

an X-ray powder diffraction pattern having peaks selected from 4.5, 7.8, 18.3 and 19.8° 2θ±0.2° 2θ;

an X-ray powder diffraction pattern similar to FIG. 1;

an infrared spectrum having at least four peaks selected from the peaks at 1625, 1597, 1429, 1307, 1280, 1224, 1166 and 1050 $cm^{-1}$±1 $cm^{-1}$; or an infrared spectrum similar to FIG. 2.

2. A cannabigerol proline cocrystal of claim 1, wherein the cannabigerol proline cocrystal is 1:2 cannabigerol L-proline cocrystal.

3. A cannabigerol proline cocrystal of claim 1, wherein the cannabigerol proline cocrystal is 1:2 cannabigerol D-proline cocrystal.

4. A cannabigerol proline cocrystal of claim 1, wherein the cannabigerol proline cocrystal is 1:2 cannabigerol D,L-proline cocrystal.

5. A pharmaceutical composition comprising a cannabigerol proline cocrystal of claim 1 and a pharmaceutically acceptable excipient.

* * * * *